United States Patent
Mäki-Ikola

(10) Patent No.: US 6,335,371 B1
(45) Date of Patent: Jan. 1, 2002

(54) METHOD FOR INDUCING COGNITION ENHANCEMENT

(75) Inventor: Outi Mäki-Ikola, Turku (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/722,262

(22) Filed: Nov. 28, 2000

(51) Int. Cl.$^7$ .................................... A61K 31/135
(52) U.S. Cl. ............................ 514/646; 514/650
(58) Field of Search ........................... 514/646, 650

(56) References Cited

U.S. PATENT DOCUMENTS 5,652,270 A    7/1997   Budai et al.

OTHER PUBLICATIONS

Bojiti et al., "Pharmacokinetics of deramciclane in dogs", Pharmaceutical Sciences, vol. 3, pp. 503–506 (1997).
Csala et al., "Decrease of gluconeogenesis by deramciclane is counteracted by cytochrome P450 inhibitors", Pharmaceutical sciences, vol. 3, pp. 469–472 (1997).
Hazai et al., "Whole–body autoradiography and quantitative organ–level distribution study of deramciclane in rats", Journal of Pharmacy and Pharmacology, vol. 51, pp. 165–174 (1999).
Kanerva H., "Pharmacokinetic studies on deramciclane", Kuopio, Department of Pharmaceutics, University of Kuopio (1999).
Kanerva et al., "Pharmacokinetics of deramciclane in dogs after single oral and intravenous dosing and multiple oral dosing", Biopharmaceutics and Drug Disposition, vol. 19, pp. 531–539 (1998).
Kanerva et al., "Pharmacokinetics and safety of deramciclane during multiple dosing", Int. J. Pharmacol Ther., vol. 37 (12), pp. 589–597 (1999).
Kanerva et al., "Different absorption profiles of deramciclane in man and in dog", Journal of Pharmacy and Pharmacology, vol. 50, pp. 1087–1093 (1998).
Kanerva et al., "Brain 5–HT2A receptor occupancy of deramciclane in humans after a single oral administration—a positron emission tomography study", Psychopharmacology, vol. 145, pp. 76–81 (1999).
Klebovich et al., "Comparative pharmacokinetics of deramciclane in rat, dog, rabbit and man after the administration of a single oral dose of 3 mg kg–1", Pharm Pharmacol Commun., vol. 4, pp. 129–136 (1998).
Lengyel et al., "Pharmacokinetics of deramciclane in rabbits", Arzneimittel–Forschung, vol. 48 (II), pp. 1063–1068 (1998).
Lengyel et al., "Absorption of the new anxiolytic compound deramciclane in rats, dogs, and rabbits", Arzneimittel–Forschung, vol. 48 (I), pp. 455–460 (1998).
Magyar et al., "Distribution of deramciclane (EGIS–3886) in rat brain regions", European Journal of Drug Metabolism and Pharmacokinetics, vol. 23 (2), pp. 125–131 (1998).
Nemes et al., "Oral, intraperitoneal and intravenous pharmacokinetics of deramciclane and its N–desmethyl metabolite in the rat", Journal of Pharmacy and Pharmacology, vol. 52 (1), pp. 47–51 (2000).
Visy et al., "Plasma protein binding of deramciclane in different species", Pharmaceutical Sciences, vol. 2, pp. 315–318 (1996).
Visy et al., "Covalent protein binding of a minor deramciclane metabolite in dog plasma" Pharmaceutical and pharmacological commun., vol. 4, pp. 587–590 (1998).
Bilkei–Gorzo et al., "mCPP–induced anxiety in the light–dark box in rats—a new method for screening anxiolytic activity", Psychopharmacology (Berl), vol. 136, pp. 291–298 (1998).
Borden et al., "Cloning of the human homologue of the GABA transporter GAT–3 and identification of a novel inhibitor with selectivity for this site", Receptors and channels, vol. 2, pp. 207–213 (1994).
Détári et al., "Differential EEG effects of the anxiolytic drugs, deramciclane (EGIS–3886), ritanserin and chlordiazepoxide in rats", Psychopharmacology, vol. 142, pp. 318–326 (1999).
Gacsályi et al., "Different antagonist activity of deramciclane (EGIS–3886) on peripheral and central 5–HT2 receptors", Pharmaceutical and pharmacological letters, vol. 6 pp. 82–85 (1996).
Gacsályi et al., "Psychopharmacology of a new anxiolytic agent Egyt–3886", Pharmacological research communications, vol. 20 (1), pp. 115–116 (1988).
Gacsályi et al., "Receptor binding profile and anxiolytic–type activity of deramciclane (EGIS–3886) in animal models", Drug development research, vol. 40, pp. 333–348 (1997).

(List continued on next page.)

Primary Examiner—William R. A. Jarvis
(74) Attorney, Agent, or Firm—Finnegan, Henderson, Farabow, Garrett & Dunner, L.L.P.

(57) ABSTRACT

A method for inducing cognition enhancement in a mammal by administering to the mammal an effective amount of 1,7,7-trimethylbicyclo[2.2.1]heptane derivative of Formula I

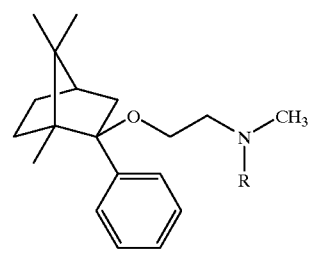

wherein R is hydrogen or methyl, or a pharmaceutically acceptable salt thereof.

24 Claims, No Drawings

OTHER PUBLICATIONS

Kõks et al., "8–OH–DPAT, but not deramciclane, antagonizes the anxiogenic–like action of paroxetine in an elevated plus–maze", Springer–Verlag (2001).

Kovács et al., "Inhibition of high–affinity synaptosomal uptake of gamma–aminobutyric acid a bicyclo–heptane derivative", Arzneim.–Forsch/Drugs Res., vol. 39 (3), pp. 295–297 (1989).

Kovács et al., "Inhibition of [3H]–D–aspartate relase by deramciclane", European journal of pharmacology, vol. 381, pp. 121–127 (1999).

Kovács et al., "Deramciclane inhibits N–methyl–D–aspartate receptor function", Brain research bulletin, vol. 52 (1), pp. 39–44 (2000).

Pälvimäki et al., "Deramciclane, a putative anxiolytic drug, is a serotonin 5–HT2C receptor inverse agonist but fails to induce 5–HT2C receptor down–regulation", Psychopharmacology, vol. 136, pp. 99–104 (1998).

Varga et al., "Effect of deramciclane, a new 5–HT receptor antagonist, on cholescystokinin–induced changes in rat gastrointestinal function", European journal of pharmacology, vol. 367, pp. 315–323 (1999).

Hazai et al., "Application of TLC–digital autoradiography as a rapid method in pilot study of deramciclane metabolism", Journal of Planar Chromatography, vol. 8, pp. 92–97 (1995).

Klebovich et al., "A sensitive, validated Gas–chromatographic bioanalytical method by nitrogen selective detection of deramciclane in dog plasma", Pharmaceutical sciences, vol. 3, pp. 497–501 (1997).

Klebovich et al., "Isolation and identification of deramciclane metabolities by OPC–(DAR) on–line sample collection combined with MS techniques", Instrumental planar chromatography, Visegrád, Hungary, (1998), Research institute for medical plants.

Klebovich et al., "TLC–DAR for the analysis of biological samples. A newly developed rapid tool for studying drug metabolism", Journal of planar chromatography, vol. 10, pp. 399–405 (1997).

Ladányi et al., "Stereochemistry and enantiomeric purity of a novel anxiolytic agent, deramciclane fumarate", Chirality, vol. 11, pp. 689–693 (1999).

Ladányi et al., "Application of overpressured layer chromatography combined with digital autodiagraphy and mass spectrometry in the study of deramciclane metabolism", Journal of AOAC international, vol. 82 (2), pp. 231–238 (1999).

Nemes et al., "A highly sensitive GC method for the determination of deramciclane and its N–desmethyl metabolite in rat and dog plasma", Methodological surveys in bioanalysis of drugs, vol. 24, pp. 103–104 (1996).

Szammer et al., "Synthesis of deramciclane labelled with radiocarbon in various positions", Journal of labeled compounds and radiopharmaceuticals, vol. 39 (12), pp. 1011–1018 (1997).

Szúnyog et al., "Comparative Bioanalytical study of 3H–deramciclane in dog plasma, using a gas chromatography–nitrogen–selective detection (GC–NPD), a new GC–radiochemical detection (GC–RD) and a liquid scintillation method", Chromatographia, vol. 48 (1/2), pp. 133–139 (1998).

Szúnyog et al., "A new tool in planar chromatography: combination of OPLC and DAR for fast separation and detection of metabolities in biological samples", Journal of planar chromatography, vol. 11, pp. 25–29 (1998).

Takács–Novák, "Potentiometric pKa determination of water–insoluble compounds: validation study in methanol/water mixtures", International journal of pharmaceuticals, vol. 151, pp. 235–248 (1997).

Takács–Novák, "A deramciklán (EGIS–3886), agy ú anxiolitikum fizikai–kémiai tulajdonságainak vizsgálata. Ionizáció és lipofilitás", Acta pharmaceutica hungarica, vol. 69, pp. 123–127 (1999).

Tolokán et al., "Determination of deramciclane and N–desmethylderamciclane in human plasma by liquid chromatography–tandem mass spectrometry using off–line robotic sample pretreatment", Journal of chromatography, vol. 896, pp. 279–290 (2000).

Kanerva et al., "The Single Dose Pharmacokinetics and Safety of Deramciclane in Healthy Male Volunteers", Biopharm. Drug Dispos., vol. 20, pp. 327–334 (1999).

Giral et al., "Reversal of Helpless Behavior in Rats by Putative 5–HT$_{1A}$ Agonists", Biol. Psychiatry, vol. 23, pp. 237–242 (1988).

Armer, "Inhibitors of Mammalian Central Nervous system Selective Amino Acid Transporters", Current Medicinal Chemistry, vol. 7, pp. 199–209 (2000).

EGYT–3886, "Drugs of the Future", vol. 15, pp. 1174–1175 (1990).

METHOD FOR INDUCING COGNITION ENHANCEMENT

FIELD OF THE INVENTION

The present invention relates in general to a method for inducing cognition enhancement in a mammal. More particularly, the invention relates to a method for inducing cognition enhancement in a mammal by administering to the mammal an effective amount of 1,7,7-trimethylbicyclo[2.2.1]heptane derivative of Formula I

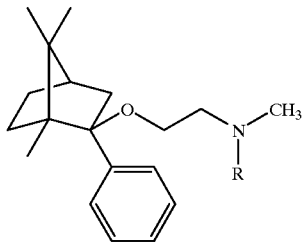

wherein R is hydrogen or methyl, or a pharmaceutically acceptable salt thereof.

The present invention also relates to a method of treating cognitive impairment in a mammal, such as, but not limited to the cognitive impairment associated with somatic diseases, psychiatric disorders and aging by administering to the mammal an effective amount of the compound of formula (I) or a pharmaceutically acceptable salt thereof.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

BACKGROUND OF THE INVENTION

The active ingredients of this invention, (1R,2S,4R)-(−)-2-phenyl 2-(dimethylaminoethoxy)-1,7,7-trimethyl-bicyclo[2.2.1]heptane, known as deramciclane, and (1R,2S,4R)-(−)-2-phenyl-2-(methylaminoethoxy)-1,7,7-trimethyl-bicyclo[2.2.1]heptane, known as N-desmethylderamciclane, and their pharmaceutically acceptable acid addition salts with inorganic and organic acids generally used for the purpose, fall within the disclosures of U.S. Pat. No. 4,342,762 and International Patent Application No. WO 98/17230, respectively, which are both incorporated herein by reference.

These compounds are selective serotonin 5HT2A- and/or 5HT2C-receptor antagonists. They have shown anxiolytic-like effects in animal test models.

DESCRIPTION OF THE INVENTION

Applicants have surprisingly discovered that the compounds of formula (I) do induce cognition enhancement in a mammal. Accordingly, an object of the present invention is a method for inducing cognition enhancement in a mammal by administering to the mammal an effective amount of a compound of Formula (I) or a pharmaceutically acceptable salt thereof. In addition, the present invention provides a method of treating cognitive impairment in a mammal associated with somatic diseases, psychiatric disorders and aging by administering to the mammal an effective amount of a compound of Formula (I) or a pharmaceutically acceptable salt thereof. Somatic diseases, such as but not limited to dementias (e.g. Lewy body dementia, vascular dementia, Alzheimer's Disease, and HIV associated dementia) and Parkinson's Disease, are associated with serious impairment in cognitive function. Cognitive impairment is related also to several psychiatric disorders, especially to affective disorders (e.g. depression, psychotic disorders, such as schizophrenia) and anxiety disorders. Anxiety disorders include but are not limited to Generalized Anxiety Disorder (GAD), Obsessive Compulsive Disorder (OCD), Post-Traumatic Stress Disorder (PTSD), Social Anxiety Disorder (SAD), Panic Disorder (PD), agarophobia, and Attention Deficit Hyperactivity Disorder (ADHD). In addition, cognition impairment is caused by several disorders associated with aging, such as Age Associated Memory Impairment. Further, cognitive impairment is often related to the usage of drugs, such as benzodiazepines and tricyclic antidepressants, which are common in the treatment of different somatic diseases and psychiatric disorders.

For the purposes of this disclosure and claims the term "treatment" is relating to treatment in order to cure or alleviate the disease or its symptoms, and to treatment in order to prevent the development or the exacerbation of the disease or its symptoms.

Pharmaceutically acceptable salts of the compound of Formula (I) can be formed with inorganic acids, e.g. hydrohalogenic acid such as hydrochloride acid or hydrobromic acid, sulfuric acid, phosphoric acid or nitric acid, or organic acids e.g., tartaric acid, succinic acid, maleic acid, maleic acid, fumaric acid, citric acid, or lactic acid. Salt with fumaric acid is preferred.

Pharmaceutical compositions containing a compound of Formula (I) or a pharmaceutically acceptable salt thereof as the active ingredient include the usual oral dosage forms, such as tablets, capsules, and liquid preparations. In oral dosage forms, the active ingredient can be mixed with suitable pharmaceutically acceptable excipients, such as starch, lactose, sucrose and magnesium stearate, in accordance with conventional pharmaceutical practice.

The precise amount of the drug to be administered to a mammal for inducing cognition enhancement and for the treatment of cognitive impairment is dependent on numerous factors known to one skilled in the art, such as the compound to be administered, the general condition of the patient, the condition to be treated etc. For example, the usual recommended oral daily dose of deramciclane would be about 5–150 mg/day, preferably 30–60 mg/day.

The invention will be further clarified by the following example, which is intended to be purely exemplary of the invention.

EXAMPLE

The cognition enhancement properties of deramciclane were studied in a randomised placebo-controlled double-blind study. The subjects were randomly assigned to four parallel groups to receive one tablet twice daily (b.i.d) of a placebo, 5 mg (=10 mg/day), 15 mg (=30 mg/day), or 30 mg (=60 mg/day) deramciclane. The study started with a one-week placebo run-in period, followed by an eight-week placebo-controlled active treatment and a two-week placebo washout period.

The efficacy of deramciclane on cognition enhancement was studied using the cognitive part of Hamilton Anxiety Scale (HAM-A) which consists of the concentration and memory items. Cognition enhancement was also assessed using Udvalg for Kliniske Undersogelser (UKU) scale.

RESULTS

Administration of deramciclane improved the cognition when measured by the cognitive part of the HAM-A. This improvement was statistically significant (p=0.04, Cochran-Mantel-Haenszel statistics) in group receiving deramciclane 15 mg b.i.d when compared to placebo in the cognitive part of the HAM-A scale. The results are presented in Table 1.

In addition, when the UKU-scale was used, there was a statistically significant positive correlation in the trend analysis indicating dose-response relationship with regard to concentration difficulties. The difference between the group receiving deramciclane 15 mg b.i.d and placebo group was statistically significant (p=0.01). The results are presented in Table 2.

TABLE 1

Hamilton Anxiety Scale/Intellectual, cognitive

|  | Placebo | 5 mg b.i.d | 15 mg b.i.d. | 30 mg b.i.d. |
|---|---|---|---|---|
| Baseline |  |  |  |  |
| Not Present | 1 (2%) | 3 (6%) | 3 (6%) | 3 (6%) |
| Mild | 13 (26%) | 17 (31%) | 12 (24%) | 15 (28%) |
| Moderate | 33 (66%) | 33 (61%) | 35 (69%) | 28 (53%) |
| Severe | 3 (6%) | 1 (2%) | 1 (2%) | 7 (13%) |
| After 8 weeks |  |  |  |  |
| Not Present | 12 (29%) | 15 (35%) | 21 (48%) | 22 (48%) |
| Mild | 20 (48%) | 20 (47%) | 19 (43%) | 14 (30%) |
| Moderate | 10 (24%) | 6 (14%) | 3 (7%) | 10 (22%) |
| Severe | 0 | 2 (5%) | 1 (2%) | 0 |

TABLE 2

UKU-scale/concentration difficulties

|  | Placebo | 5 mg b.i.d | 15 mg b.i.d. | b.i.d. |
|---|---|---|---|---|
| Baseline |  |  |  |  |
| Normal | 4 (8%) | 8 (5%) | 4 (8%) | 3 (6%) |
| Mild | 15 (29%) | 15 (28%) | 16 (30%) | 16 (30%) |
| Moderate | 28 (55%) | 30 (56%) | 32 (60%) | 31 (57%) |
| Severe | 4 (8%) | 1 (2%) | 1 (2%) | 4 (7%) |
| After 8 weeks |  |  |  |  |
| Normal | 12 (29%) | 15 (35%) | 24 (55%) | 23 (50%) |
| Mild | 19 (45%) | 19 (44%) | 16 (36%) | 14 (30%) |
| Moderate | 10 (24%) | 9 (21%) | 3 (7%) | 9 (20%) |
| Severe | 1 (2%) | 0 | 1 (2%) | 0 |

Although the invention has been illustrated by the preceding example, it is not to be construed as being limited to the materials employed therein; rather, the invention is directed to the generic area as herein disclosed. Various modifications and embodiments thereof can be made without departing from the spirit or scope thereof.

I claim:

1. A method of inducing cognition enhancement in a mammal, comprising administering to said mammal an effective amount of a compound of Formula (I)

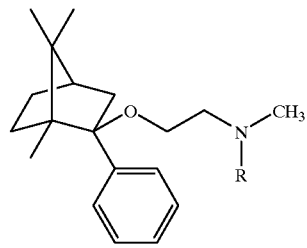

wherein R is hydrogen or methyl, or a pharmaceutically acceptable salt thereof.

2. The method of claim 1, wherein the mammal is human.

3. The method of claim 1, wherein the compound is deramciclane or a pharmaceutically acceptable salt thereof.

4. The method of claim 1, wherein about 5–150 mg/day of the compound of Formula (I) or pharmaceutically acceptable salt thereof is administered.

5. The method of claim 4, wherein about 10–60 mg/day of the compound of Formula (I) or pharmaceutically acceptable salt thereof is administered.

6. The method of claim 5, wherein about 30 mg/day of the compound of Formula (I) or pharmaceutically acceptable salt thereof is administered.

7. A method of treating cognitive impairment in a mammal, comprising administering to said mammal an effective amount of a compound of Formula (I)

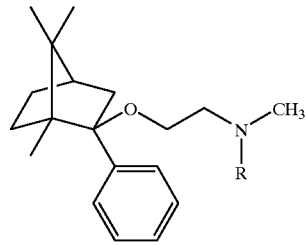

wherein R is hydrogen or methyl, or a pharmaceutically acceptable salt thereof.

8. The method of claim 7, wherein the cognitive impairment is associated with Parkinson's Disease.

9. The method of claim 7, wherein the cognitive impairment is associated with dementias.

10. The method of claim 7, wherein the cognitive impairment is associated with an anxiety disorder.

11. The method of claim 10, wherein the anxiety disorder is Generalized Anxiety Disorder.

12. The method of claim 10, wherein the anxiety disorder is Obsessive Compulsive Disorder.

13. The method of claim 10, wherein the anxiety disorder is Post-Traumatic Stress Disorder.

14. The method of claim 10, wherein the anxiety disorder is Social Anxiety Disorder.

15. The method of claim 10, wherein the anxiety disorder is Panic Disorder.

16. The method of claim 10, wherein the anxiety disorder is agarophobia.

17. The method of claim 7, wherein the cognitive impairment is associated with Age Associated Memory Impairment.

18. The method of claim 7, wherein the cognitive impairment is associated with depression.

19. The method of claim 7, wherein the cognitive impairment is associated with the usage of benzodiazepines.

20. The method of claim 7, wherein the cognitive impairment is associated with the usage of tricyclic antidepressants.

21. The method of claim 7, wherein the compound is deramciclane or a pharmaceutically acceptable salt thereof.

22. The method of claim 7, wherein about 5–150 mg/day of the compound of Formula (I) or pharmaceutically acceptable salt thereof is administered.

23. The method of claim 22, wherein about 10–60 mg/day of the compound of Formula (I) or pharmaceutically acceptable salt thereof is administered.

24. The method of claim 23, wherein about 30 mg/day of the compound of Formula (I) or pharmaceutically acceptable salt thereof is administered.

* * * * *